United States Patent
Son et al.

(10) Patent No.: US 8,635,911 B2
(45) Date of Patent: Jan. 28, 2014

(54) APPARATUS AND METHOD FOR MEASURING BUOYANT MASS AND DEFORMABILITY OF SINGLE CELLS

(75) Inventors: Sungmin Son, Cambridge, MA (US); Sangwon Byun, Cambridge, MA (US); Andrea Kristine Bryan, Allston, MA (US); Thomas Burg, Goettingen (DE); Amneet Gulati, Cambridge, MA (US); Jungchul Lee, Seoul (KR); Scott Manalis, Cambridge, MA (US); Yao-Chung Weng, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 278 days.

(21) Appl. No.: 13/096,248

(22) Filed: Apr. 28, 2011

(65) Prior Publication Data
US 2012/0118063 A1 May 17, 2012

Related U.S. Application Data

(60) Provisional application No. 61/331,470, filed on May 5, 2010.

(51) Int. Cl.
*G01H 13/00* (2006.01)
*C12M 1/34* (2006.01)
*C12M 3/00* (2006.01)

(52) U.S. Cl.
USPC ............................ 73/579; 435/29; 435/287.1

(58) Field of Classification Search
USPC .......................................................... 73/579
See application file for complete search history.

(56) References Cited

U.S. PATENT DOCUMENTS

| 7,282,329 B2 | 10/2007 | Manalis et al. | |
|---|---|---|---|
| 2004/0035426 A1* | 2/2004 | Curran et al. | 128/206.19 |
| 2005/0064581 A1 | 3/2005 | Manalis et al. | |
| 2008/0247911 A1* | 10/2008 | Manalis | 422/82.05 |
| 2009/0053749 A1 | 2/2009 | Manalis et al. | |
| 2010/0154535 A1* | 6/2010 | Manalis et al. | 73/32 R |

FOREIGN PATENT DOCUMENTS

| WO | WO 2007081902 A2 * | 7/2007 |
| WO | WO 2008045988 A1 * | 4/2008 |
| WO | WO 2009035125 A1 * | 3/2009 |

OTHER PUBLICATIONS

"Biomechanics and biophysics of cancer cells" by Subra Suresh, Acta Biomaterialia 3 (2007) 413-438.
Rosenbluth et al., "Analyzing cell mechanics in hematologic diseases with microfluidic biophysical flow cytometry," Lab Chip, vol. 81, No. 7, Jul. 2008, pp. 993-1228.

(Continued)

*Primary Examiner* — Peter Macchiarolo
*Assistant Examiner* — Rose M Miller
(74) *Attorney, Agent, or Firm* — Sam Pasternack; MIT Technology Licensing Office

(57) ABSTRACT

Method for determining buoyant mass and deformability of a cell. The method includes introducing the cell into a suspended microchannel resonator that includes a constriction near a distal location in the resonator. A first frequency shift in the resonator is monitored as a cell moves to the distal location in the resonator, the first frequency shift being related to the buoyant mass of the cell. Transit time of the cell through the constriction is measured by monitoring a second frequency shift as a result of a change in cell location as it passes through the constriction, whereby deformability is determined from the measured buoyant mass and transit time.

3 Claims, 4 Drawing Sheets

(56) References Cited

OTHER PUBLICATIONS

Hirose et al., "A New Stiffness Evaluation toward High Speed Cell Sorter," 2010 IEEE International Conference on Robotics and Automation, May 2010.

Hou et al., "Deformability study of breast cancer cells using microfluidics," Biomed Microdevices, vol. 11, No, 3, Jun. 2009, pp. 557-564.

Burg et al., "Weighing of biomolecules, single cells and single nanoparticles in fluid," Nature 446 (7139), 1066-1069 (2007).

International Search report and Written Opinion issued in Connection with International Patent Application No. PCT/US2011/034943 mailed on Nov. 15, 2012.

Suresh et al.: "Biomechanics and biophysics of cancer cells", Acta Materialia, vol. 55, No. 12, Jun. 8, 2007, pp. 3989-4014.

* cited by examiner

APPARATUS AND METHOD FOR MEASURING BUOYANT MASS AND DEFORMABILITY OF SINGLE CELLS

This application claims priority to U.S. provisional application Ser. No. 61/331,470 filed May 5, 2010. The contents of this provisional application are incorporated herein by reference in their entirety.

This invention was made with government support under Grant Nos. R01-GM085457 and U54-CA143874 awarded by the NIH. The government has certain rights in the invention.

BACKGROUND OF THE INVENTION

This invention relates to measuring cell physical properties and more particularly to using a suspended microchannel resonator to determine cell buoyant mass and deformability.

It is known that the transit time of a cell through a pore depends on the physical properties of the cell. Theoretical analyses have also shown that transit time depends on the cell's size and deformability. Transit times are altered in sepsis, a process in which inflammatory mediators in the bloodstream activate neutrophils, and in leukostasis, an often fatal and poorly understood complication of acute leukemia.

A cell's mechanical property such as deformability can also provide a window on how disease states influence a single cell's biomechanics. For example, studies have examined the effect of a malaria-producing parasite on deformability of human red blood cells. See, "Biomechanics and biophysics of cancer cells" by Subra Suresh, Acta Biomaterialia 3 (2007) 413-438. It is also known that the deformability of cancer cells has implications for cell signaling, cytoadherence, migration, invasion and metastatic potential. Therefore, knowledge of a cell's deformability is important for selecting appropriate diagnostic and treatment protocols.

Cell mechanical properties have been determined using atomic force microscopes, laser/optical tweezers, mechanical microplate stretchers, micro-postarray deformation with patterned microarrays that serve as cell substrates and micropipette aspiration. These techniques are limited by relatively low throughput.

Microfluidic and nanofluidic assays using rigid or compliant channels have also been used to simulate the flow of cells through blood vessels, and in conjunction with quantitative cell deformability assays, such as optical tweezers, to study the elastic and viscoelastic characteristics of cells. See, Rosenbluth et al., "Analyzing cell mechanics in hematologic diseases with microfluidic biophysical flow cytometry," Lab Chip, Volume 81, No. 7, July 2008, pp 993-1228; and Hirose, et al., "A New Stiffness Evaluation toward High Speed Cell Sorter," 2010 IEEE International Conference on Robotics and Automation, May, 2010. See also, Hou et al., "Deformability study of breast cancer cells using microfluidics," Biomed Microdevices, Volume 11, No. 3, June 2009, pp 557-564. The contents of all of the references cited herein are incorporated by reference in this application in their entirety.

It is therefore an object of the present invention to provide a high-throughput system for determining a cell's buoyant mass and deformability that enables the dependencies of transit time through a constriction on deformability and size to be decoupled using a suspended microchannel resonator.

SUMMARY OF THE INVENTION

In a first aspect, the invention is a method for determining buoyant mass and deformability of a cell including introducing the cell into a suspended microchannel resonator that includes a constriction near a distal location in the resonator. A first frequency shift in the resonator is monitored as the cell moves to the distal location in the resonator, the first frequency shift being related to the buoyant mass of the cell. Transit time of the cell through the constriction is measured by monitoring a second frequency shift as a result of a change in cell location as it passes through the constriction whereby deformability is determined from the measured buoyant mass and transit time. In a preferred embodiment, the constriction is sized to deform the cell as it passes through the constriction.

In another aspect, the invention is apparatus for determining the buoyant mass and deformability of a cell including a suspended microchannel resonator having a constriction near a distal end of the resonator. Means are provided for monitoring a first frequency shift in the resonator as a cell moves to the distal location in the resonator, the first frequency shift being related to the buoyant mass of the cell. Means are also provided for measuring the entry time and the transit time of the cell through the constriction by monitoring a second frequency shift as a result of a change in cell location as it passes through the constriction whereby deformability is determined from the measured buoyant mass and transit time.

DESCRIPTION OF THE PREFERRED EMBODIMENT

The present invention employs a suspended microchannel resonator to measure buoyant mass and deformability of single cells. Suspended microchannel resonators are well-known for providing an extremely accurate way to measure particle masses. In a suspended microchannel resonator, as a particle or cell traverses the resonator, the vibrational frequency shifts depending on the mass of the particle to be measured. See, U.S. Pat. No. 7,282,329 and Burg, et al., "Weighing of biomolecules, single cells and single nanoparticles in fluid," Nature 446 (7139), 1066-1069 (2007). The contents of this patent and article are incorporated herein by reference in their entirety.

Figure 1:
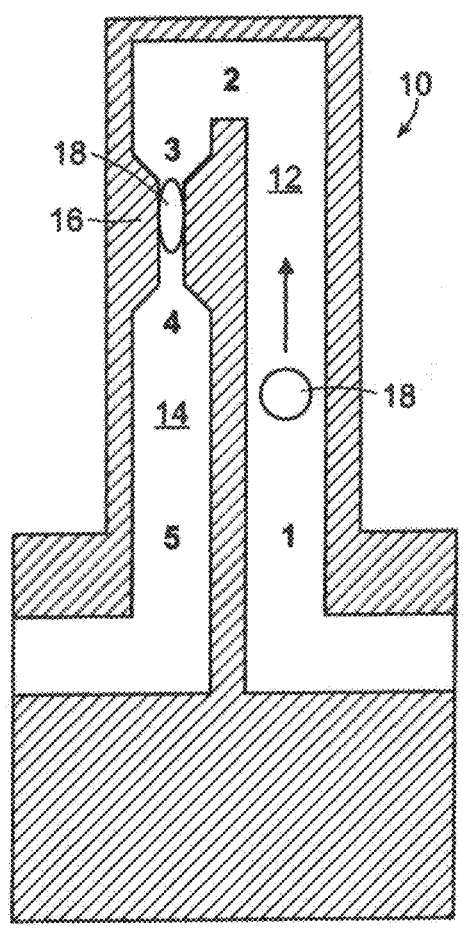
FIG. 1 is a schematic illustration of an embodiment of the invention disclosed herein.

In the present invention, a suspended microchannel resonator is used not only to measure the mass of a cell but also to determine the cell's deformability. With reference to FIG. 1, a suspended microchannel resonator 10 includes channels 12 and 14. The channel 14 includes a constriction 16. A cell 18 is introduced into the suspended microchannel resonator 10 and proceeds from position 1 to position 2. Thereafter the cell 18 enters the constriction 16 at location 3. The cell 18 then proceeds to locations 4 and 5.

Figure 2:
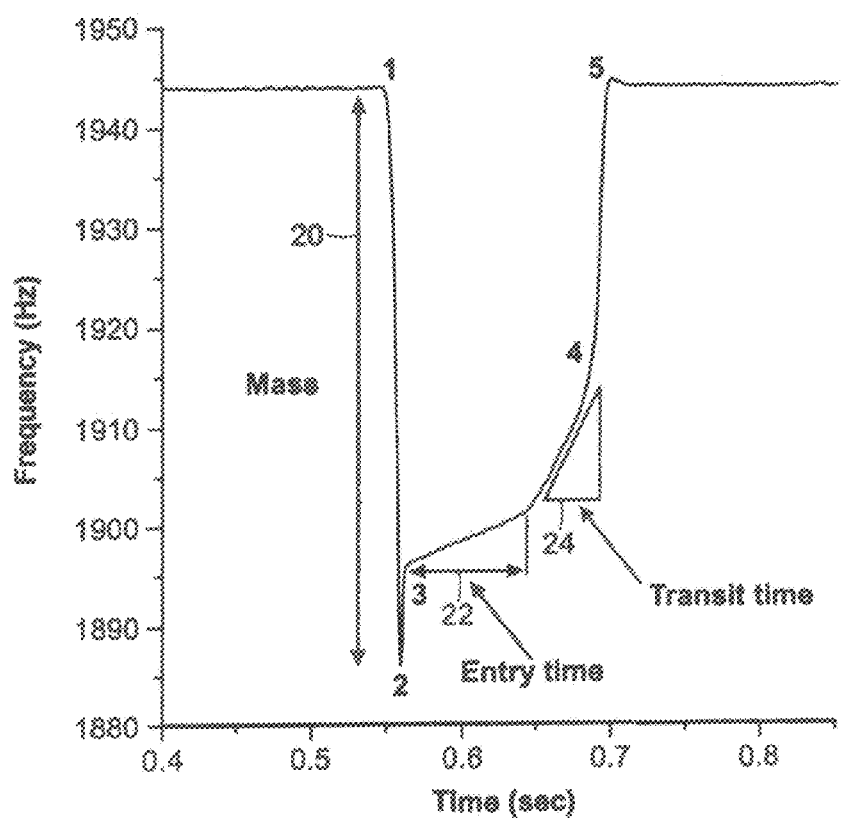
FIG. 2 is a graph of frequency versus time illustrating frequency shifts related to a cell's mass and cell deformability.

With reference now both to FIGS. 1 and 2, when the cell 18 passes from station 1 to station 2, the vibrational frequency of the suspended microchannel resonator 10 shifts as shown at 20 in FIG. 2. The amount of frequency shift is related to the cell's mass. The cell 18 mass relates to cell size and the entry time and the transit time through the constriction 16 depends on cell size in addition to its deformability.

With reference still to FIG. 2, the time for entry of the cell 18 into the constriction 16 is shown at 22. The transit time of the cell 18 fully through the constriction is shown as the transit time 24.

In operation, the cell 18 is introduced into the suspended microchannel resonator 10 and proceeds from location 1 to location 2 while the frequency of the resonator 10 is monitored. The shift in frequency from station 1 to station 2 is an indication of the cell's mass. The cell's mass is also related to cell size. The cell proceeds from station 2 to station 3 that is the entry into the constriction 16 and provides an entry time 22. The cell 18 proceeds through the constriction 16 passing stations 4 and 5 that then provide the transit time 24 through the constriction. It is known that a suspended microchannel resonator can resolve a cell's position with the precision of 10-100 nm. Thus, the approach disclosed herein offers advantages in terms of sensitivity and simplicity when compared to optical tracking methods. The resonator 10 is able to measure the cell's buoyant mass with high precision (near 0.01 percent) immediately before it passes through the constriction 16. The measurements enable the transit time dependencies on deformability and size to be decoupled. Throughput of the system disclosed herein can approach 1000 cells per hour.

Figure 3:
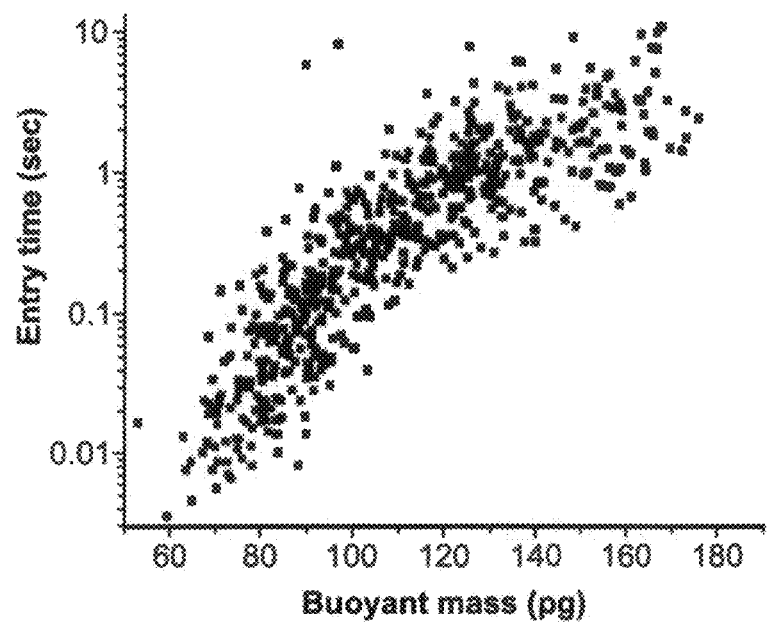
FIG. 3 is a graph of entry time versus buoyant mass for a cell line derived from a mouse model of lung adenocarcinoma.
Figure 4:
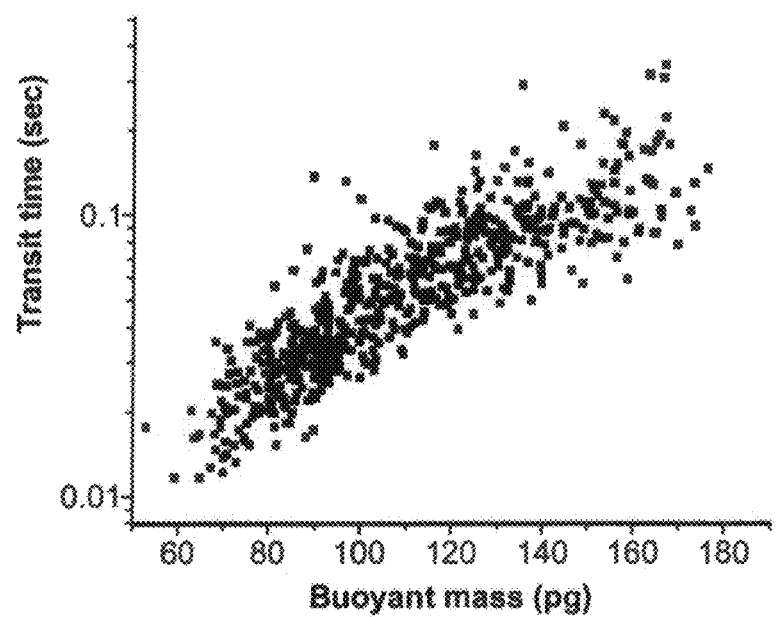
FIG. 4 is a graph of transit time versus buoyant mass also from the mouse model of lung adenocarcinoma.

Experiments have been performed on a cell line derived from a mouse model of lung adenocarcinoma developed by the Jacks Laboratory. FIG. 3 is a graph of entry time versus buoyant mass for such cells. FIG. 4 is a graph of total time versus buoyant mass as a cell proceeds from station 3 to station 5.

Figure 5:
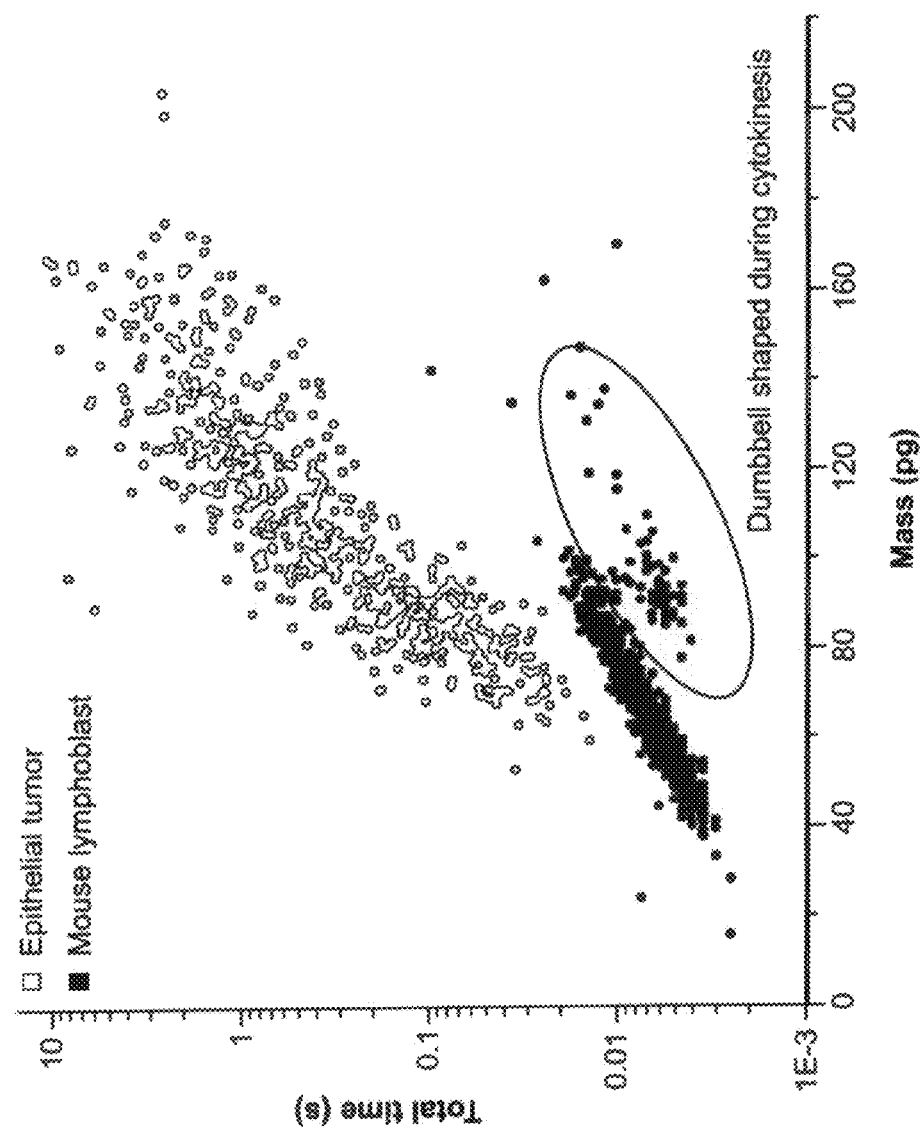
FIG. 5 is a graph of total transit time versus mass for epithelial tumor cells and mouse lymphoblasts.

FIG. 5 shows the results of an experiment using epithelial tumor cells and mouse lymphoblasts, The upper cluster in FIG. 5 relates to epithelial tumor cells and the lower cluster resulted from experiments with the mouse lymphoblasts.

It is thus seen that a suspended microchannel resonator, modified to include a constriction, can determine not only a particle's mass very accurately, but can also determine the particle's deformability since mass can be used to correlate with cell size. Therefore, both particle mass and deformability can be determined from a single pass through the suspended microchannel resonator including a constriction as disclosed herein.

It is recognized that modifications and variations of the present invention will occur to those with ordinary skill in the art and it is intended that all such modifications and variations be included within the scope of the appended claims.

What is claimed is:

1. Method for determining buoyant mass and deformability of a cell comprising:
    introducing the cell into a suspended microchannel resonator that includes a channel around the periphery of the resonator, the channel having a constriction along the edge of the resonator near a distal location in the resonator;
    monitoring a first frequency shift in the resonator as the cell moves to the distal location in the resonator, the first frequency shift being related to the buoyant mass of the cell; and
    measuring transit time of the cell through the constriction by monitoring a second frequency shift as a result of a change in cell location as it passes through the constriction, whereby deformability is determined from the measured buoyant mass and transit time.

2. The method of claim 1 wherein the constriction is sized to deform the cell.

3. Apparatus for determining buoyant mass and deformability comprising:
    a suspended microchannel resonator including a channel around the periphery of the resonator, the channel having a constriction along the edge of the resonator near a distal location of the resonator;
    means for monitoring a first frequency shift in the resonator as a cell moves to the distal location in the resonator, the first frequency shift being related to the buoyant mass of the cell; and
    means for measuring an entry time and a transit time of the cell through the constriction by monitoring a second frequency shift as a result of a change in cell location as it passes through the constriction, whereby deformability is determined from the measured buoyant mass and transit time.

\* \* \* \* \*